United States Patent [19]

Frangatos et al.

[11] Patent Number: 4,661,273

[45] Date of Patent: Apr. 28, 1987

[54] MERCAPTO-THIADIAZOLE REACTION PRODUCTS AS MULTIFUNCTIONAL LUBRICANT ADDITIVES AND COMPOSITIONS THEREOF

[75] Inventors: Gerassimo Frangatos, Haddonfield; Robert H. Davis, Pitman, both of N.J.

[73] Assignee: Mobil Oil Company, New York, N.Y.

[21] Appl. No.: 814,428

[22] Filed: Dec. 30, 1985

[51] Int. Cl.$^4$ .......................................... C10M 133/00
[52] U.S. Cl. .................................... 252/47; 252/47.5; 548/142
[58] Field of Search .................. 252/47, 47.5; 548/142

[56] References Cited

U.S. PATENT DOCUMENTS

| | | | |
|---|---|---|---|
| 2,719,126 | 9/1955 | Fields et al. | 252/47 |
| 2,799,651 | 7/1957 | Richardsen et al. | 252/47.5 |
| 3,663,561 | 5/1972 | Blaha | 252/47 |
| 3,896,050 | 7/1975 | White | 252/47 |
| 4,410,703 | 10/1983 | Okorodudu | 252/47.5 |

*Primary Examiner*—William R. Dixon, Jr.
*Assistant Examiner*—Cynthia A. Prezlock
*Attorney, Agent, or Firm*—Alexander J. McKillop; Michael G. Gilman; Howard M. Flournoy

[57] ABSTRACT

Zinc/phosphorus-free antiwear agents and antioxidants are provided by reaction products of 2,5-dimercapto-1,3,4-thiadiazole with mercaptans and thionyl chloride.

34 Claims, No Drawings

MERCAPTO-THIADIAZOLE REACTION PRODUCTS AS MULTIFUNCTIONAL LUBRICANT ADDITIVES AND COMPOSITIONS THEREOF

BACKGROUND OF THE INVENTION

This invention is directed to reaction products of mercapto-thiadiazoles, mercaptans and thionyl chloride as zinc/phosphorus-free antiwear agents and antioxidants.

Replacement of zinc phosphorodithioates by zinc/phosphorus-free antiwear additives in circulating oils, gear oils and various other lubricating systems is considered highly desirable because of environmental considerations and the potential electrolytic corrosivity of zinc salts. An additive system which in addition to antiwear activity exhibits antioxidant activity and copper passivation is highly desirable. The condensates of the present invention provide outstanding FZG gear performance, low Four-ball wear and antioxidant activity. Furthermore, they contain no corrosive sulfur.

Various reaction products of mercapto and dimercapto-thiadiazoles (DMTD) are known in the art. For example, reaction products of 2,5-dimercapto-1,3,4-thiadiazole are disclosed in U.S. Pat. No. 4,128,510 as being useful as cross-linking agents for halogen-containing polymers. U.S. Pat. No. 4,382,869 discloses reaction products of mercaptothiadiazoles with hydroxyl-containing compounds as friction reducing and corrosion-inhibiting additives for lubricant oils. Although reaction products containing the mercapto-1,3,4-thiadiazole structure has found widespread use as lubricant antioxidants and metal passivators, the compositions and the utility of the reaction products described in this patent application are believed to be unknown heretofore in the art.

SUMMARY OF THE INVENTION

In accordance with the present invention there are provided lubricant compositions comprising a lubricant and an antiwear/EP and/or antioxidant amount of a product of reaction made by reacting a mercapto-thiadiazole with a mercaptan and thionyl chloride. The reaction may take place in the presence of a suitable stabilizing or dispersing agent or said agent may be contacted at the conclusion of the reaction. The invention is also directed to the reaction products thereof.

DESCRIPTION OF SPECIFIC EMBODIMENTS

The synthesis and evaluation of derivatives of mercapto thiadiazoles, particularly 2,5-dimercapto-1,3,4 thiadiazole (DMTD) as potential no-phosphorus multifunctional additives and replacement for Zn phosphorodithioates in circulating oils, gear oils, and other lubricating systems is an attractive and novel route for obtaining these goals.

In general, the additive products of the invention are synthesized by the condensation of a mercapto-thiadiazole, for example, 2,5-dimercapto-1,3,4-thiadiazole with mercaptans and thionyl chloride (SOCl$_2$).

Any appropriate mercapto-thiadiazole may be used herein. Some suitable examples include but are not limited to 3,4-dimercapto-1,2,5-thiadiazole, 3,5-dimercapto-1,2,4-thiadiazole, 4,5-dimercapto-1,2,5-thiadiazole, 4,5-dimercaptobenzo 1,2,3-thiadiazole, 4,7-dimercaptobenzo 1,2,3-thiadiazole, 4,6-dimercaptobenzo 1,2,3-thiadiazole, 5,6-dimercaptobenzo 1,2,3-thiadiazole, 5,7-dimercaptobenzo 1,2,3-thiadiazole, 6,7-dimercaptobenzo 1,2,3-thiadiazole, 4,5-dimercaptobenzo 2,1,3-thiadiazole, 4,6-dimercaptobenzo 2,1,3-thiadiazole, 5,6-dimercaptobenzo 2,1,3-thiadiazole, 5,7-dimercaptobenzo 2,1,3-thiadiazole, 6,7-dimercaptobenzo 2,1,3-thiadiazole. Especially preferred is 2,5-dimercapto-1,3,4-thiadiazole.

Suitable mercaptans include but are not limited to $C_1$ to about $C_{22}$ alkyl mercaptans. Especially preferred are t-nonyl and hexadecyl mercaptans.

Optionally a stabilizing or dispersing agent may be used in the synthesis process. The reaction process in accordance with the invention may be carried out in the presence of such agent or the product of reaction thereof may be treated with such agent. Any suitable agent known in the art that would disperse the reaction medium and stabilize the products without having a detrimental effect upon the desired reaction may be used. Particularly qualified are thiadiazoles such as 2,5-bis(t-nonyl-thio)-1,3,4-thiadiazole and non-emulsive amines such as Primene 81R amine. Generally any t-alkylthio-thiadiazole may be used. Primene 81R amine is a particularly preferred non-emulsive amine. It is believed to be a mixture of primary aliphatic amines of predominantly $C_{12}$ to $C_{14}$ t-alkyl groups. It is more fully reported in U.S. Pat. No. 3,224,957.

The reaction conditions are based primarily on the particular reactants. Usually, however, the temperature may vary from about 50° to about 120° C., pressure from ambient to higher if desired, time from about 1 to about 8 hours or more depending on specific reactants.

The molar ratio of reactants varies DMTD/mercaptan/thionylchloride of from about 1:2:1.5 to about 1:12:8. The amount of stabilizing or dispersing agent when used may vary from about 5 to about 60 wt.% based on the weight of the condensation product. Preferably from about 10 to about 50 wt.% is used.

The lubricants which may be used with the additives (reaction products) of this invention are mineral and synthetic lubricating oils, mixtures thereof and greases made therefrom. The mineral oils will be understood to include not only the paraffinic members, but also the naphthenic members. By synthetic oils are meant synthetic hydrocarbons, polyalkylene oxide oils, polyacetals, polysilicones and the like, as well as synthetic ester oils. Included among the latter type are those esters made from monohydric alcohols and polycarboxylic acids, such as 2-ethyl-hexylazelate and the like. Also included are those esters made from polyhydric alcohols and aliphatic monocarboxylic acids. Those of this group are especially important and in this group are found esters prepared from (1) the trimethylols, such as the ethane, propane and butane derivatives thereof, (2) 2,2-disubstituted propane diols and (3) the pentaerythritols reacted with aliphatic monocarboxylic acids containing from about 4 to 9 carbon atoms. Mixtures of these acids may be used to prepare the esters. Preferred among the esters are those made from pentaerythritol and a mixture of $C_5$–$C_9$ acids.

As has been disclosed hereinabove, the reaction products are useful as antiwear/EP and antioxidant agents. They are added to the lubricating medium in amounts sufficient to impart such properties to the lubricant. More particularly, such properties will be imparted to the lubricant by adding from about 0.01% to about 10% by weight, preferably from about 0.01% to about 3%, of the neat product.

Having discussed the invention in broad and general terms, the following are offered to illustrate it. It is to be understood that the examples are merely illustrative and are not intended to limit the scope of the invention.

EXAMPLE 1

DMTD, SOCl$_2$ and t-nonylmercaptan condensate (molar ratio 1:2.2:2) in 2,5-bis(t-nonylthio)-1,3,4-thiadiazole dispersing medium (50 wt.%).

50 gms of 2,5-bis(t-nonylthio)-1,3,4-thiadiazole, t-nonylmercaptan (32 gms., 0.2 mole) and DMTD (2,3-dimercapto-1,3,4-thiadiazole; 15 gms., 0.1 mole) are placed in a flask equipped with dropping funnel, reflux condenser, thermometer, mechanical stirrer, a nitrogen inlet tube and outlet tube leading from the condenser to scrubbers containing aqueous NaOH solution. the reaction system is protected from exposure to moist air by means of drying tubes.

The mixture is heated to 85° C. with stirring under a dry nitrogen stream. SOCl$_2$ (26.18 gms.; 0.22 mole) is cautiously added dropwise over a period of thirty minutes. The reaction is strongly exothermic and is able to retain the temperature of the reaction mixture at 85°-88° C. without external heating throughout most of the addition period. the reaction mixture which is a homogeneous fluid is heated at 85° C. for two additional hours after completion of the SOCl$_2$ addition. It is subsequently placed under house vacuum and heated to final temperature of 105° C. The mixture is cooled to room temperature and treated with n-hexane (300 ml). The solution is heated at 70° C. for a few minutes, is cooled and filtered. A minimal quantity of solids (0.6 g) is collected on the filter. The filtrate is mixed with 200 ml of 5 wt.% aqueous NaOH solution and warmed to 55° C. The organic layer is separated. The aqueous layer is extracted with an additional quantity of n-hexane (50 ml). The combined organic layers are washed with water, dried and stripped of solvent and volatiles under house vacuum and final pot temperature 86° C. The residue, a clear purple fluid, weighed 102.87 gms. It was readily soluble in 100 cSt oil, n-hexane, acetone, DMF but sparingly soluble in water, acetonitrile and DMSO. IR Spectrum consistent with anticipated structure of poly dithionyl sulfoxide.

EXAMPLE 2

DMTD, SOCl$_2$, t-nonylmercaptan (molar ratio 1:2.2:2) condensate treated with Primene 81R Amine (10 wt.%).

DMTD (2,3 dimercapto-1,3,4 thiadiazole; 75 g, 0.5 mole), t-nonylmercaptan (160 g, 1.0 mole) and toluene (500 ml) are placed in a flask equipped with dropping funnel, mechanical stirrer, reflux condenser, thermometer, nitrogen inlet tube and outlet tube leading from the condenser to scrubbers containing aqueous solution of NaOH. The reaction system is protected from exposure to moist air by means of drying tubes.

The mixture is heated to 75° C. (with stirring under a light stream of dry nitrogen. SOCl$_2$ (130.9 g, 1.1 mole) diluted with 150 ml of toluene is added dropwise over a period of one hour. The temperature of the reaction mixture is maintained at 75°-80° C. throughout the SOCl$_2$ addition and for two additional hours. The solvent and any volatiles present are distilled under reduced pressure-house vacuum. the final pot temperature is allowed to reach 110° C. The residue (278 gms) is cooled to room temperature and treated with one liter of n-hexane and 600 ml of 5 wt.% aqueous NaOH solution. the organic layer is separated. The aqueous layer is extracted with an additional quantity of hexane (200 ml). The combined extracts are washed with water and dried. Primene 81R amine (27.8 gms) is added. the clear solution is stripped of solvent and any volatiles under house vacuum and final pot temperature is 100° C. The residue, a clear purple fluid, weighs 288 gms. it is readily soluble in 100 cst oil, n-hexane, acetone, MEK and DMF. IR spectrum is in agreement with anticipated structure.

The condensation reaction, believed novel, is applicable over a broad spectrum of uses. The polarity of the sulfoxide groups in the vicinity of the thiadiazole moiety enhances the adhesion to metals through a potential bidentate ligant formation. This arrangement protects metal surfaces through strong adsorption-chemisorption and consequently increases the antiwear-EP activity of the aggregate.

Evaluation of Products

The examples in accordance with the invention were blended into a zinc/phosphorus-free heavy duty circulating oil formulation designated Test Oil #1 and 2 and evaluated as to gear test wear, antiwear/EP characteristics and antioxidation properties. See Tables 1 and 2.

The formulation was tested for gear wear protection according to the FZG Gear Test (DIN-51.354). In this test, dip-lubricated gears are weighed and operated at a fixed speed and fixed initial oil temperature (90° C.) in the gear oil under test. The load on the teeth is increased in increments. After each load stage, the weight changes are determined and recorded. The results are reported in Table 1 and Table 2. The higher the Fail Stage value the better the material. The lower the wear value the better the product.

The formulation was also tested for its antiwear properties according to the Four-Ball Wear Test. The results are set forth in Table 2. The products of the examples and comparative examples were tested in the 4-ball test using a modified 4-ball machine. In this test, three stationary balls are placed in a lubricant cup and a lubricant containing the additive to be tested is added thereto. A fourth ball is placed on a chuck mounted on a device which can be used to spin the ball at known speeds and loads. Various percentages by weight of each product was placed in the blend. The samples were tested at 130° F. at a load of 20 kg and 1800 rpm for 60 minutes.

The formulation was tested for its antioxidation characteristics in accordance with the Rotary Bomb Test (RBOT-ASM D-2272). The test oil, water, and copper catalyst coil, contained in a covered glass container, are placed in a bomb equipped with a pressure gauge. The bomb is charged with oxygen to a pressure of 90 psi, placed in a constant temperature oil bath set at 150° C., and rotated axially at 100 rpm at an angle of 30° from the horizontal. The time for the test oil to react with a given volume of oxygen is measured, completion of the time being indicated by a specific drop in pressure.

TABLE 1

ZINC/PHOSPHORUS - FREE HEAVY CIRCULATING OIL FORMULATIONS

| Composition | FZG Fail Stage | Wear mg |
|---|---|---|
| Reference Oils | | |

TABLE 1-continued

ZINC/PHOSPHORUS - FREE HEAVY CIRCULATING OIL FORMULATIONS

| Composition | FZG Fail Stage | Wear mg |
|---|---|---|
| ᴬTest Oil #1 - 0.25% Zn (DTP)₂ | 11 | 125 |
| – 1.00% Zn (DTP)₂ | 11 | 72 |
| Test Oil #1 less Zn (DTP)₂ | 8 | — |
| + 1% (1) | 9 | 349 |
| + 1% (2) | 10 | 118 |
| Thionyl Chloride Reaction Products | | |
| + 1% (3) | 12 | 45 |
| + 1% Ex. 1 | 12 | 40 |
| + 1% Ex. 2 | 12 | 37 |

(1) Comparative Example: sulfurized olefin
(2) Comparative Example: mercaptobenzothiazole type antiwear agent
(3) Reaction product of SOCl₂/C₉SH/DMTD without dispersing medium.

TABLE 2

ZINC/PHOSPHORUS - FREE CIRCULATING OIL FORMULATIONS

| Performance Tests | ᴬTest Oil #2 [0.09% Zn(DTP)₂] | Test Oil #2 less Zn(DTP)₂ plus: | | | |
|---|---|---|---|---|---|
| | | EXAMPLE 3 0.09% | EXAMPLE 2 0.09% | EXAMPLE 2 0.2% | EXAMPLE 1 0.2% |
| FZG Gear Test | | | | | |
| Fail Stage | 8/9 | 9 | 9 | 10 | 9 |
| Wear, mg | 20 | 30 | 51 | — | 21 |
| 4-Ball Wear Scar Diam, mm | 0.25 | 0.26 | — | 0.27 | 0.25 |
| RBOT, minutes | 225 | 365 | — | 415 | — |

(3) Reaction product of SOCl₂/C₉SH/DMTD without dispersing medium.
ᴬTest Oils #1 and #2 represent typical rust inhibited circulatory oils used to lubricate industrial equipment such as pumps, gears, etc.

From the above data it is quite clear that the reaction products (additives) of the present invention provide noticably outstanding FZG gear performance and antiwear/EP characteristics but also exhibit significant antioxidation properties.

These additives, in accordance with the invention, prepared by reaction of thionyl chloride with mercaptothiadiazole and mercaptan, provide outstanding FZG gear performance, low Four-ball wear and a boost in oxidation stability. Accordingly they show promise as replacements for zinc dithiophosphate antiwear agents used in heavy circulating oil formulations.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A product of reaction having multifunctional antiwear/EP and antioxidation characteristics prepared by reacting a mercapto or dimercapto thiadiazole with a mercaptan and thionyl chloride wherein the amount of mercapto or dimercapto-thiadiazole to thionyl chloride to mercaptan varies in a molar ratio of from 1:2:1.5 to about 1:12:8 and wherein the temperature varies from 50° to about 120° C., the pressure from ambient to about 150 psi and the time from about 1 to about 8 hours or more.

2. The product of claim 1 wherein the mercaptan is a C₁ to about a C₂₂ alkyl mercaptan.

3. The product of claim 2 wherein the mercaptan is a tertiary alkyl mercaptan.

4. The product of claim 3 wherein the mercaptan is t-nonyl mercaptan.

5. The product of claim 1 wherein the reaction is carried out in the presence of a stabilizing or dispersing agent.

6. The product of claim 1 wherein the stabilizing agent is added to the reaction medium after the reaction is substantially completed.

7. The product of claim 5 wherein said agent is an alkylthio-thiadiazole or a bis alkylthio-thiadiazole.

8. The product of claim 7 wherein said agent is 2,5-bis(t-nonylthio)-1,3,4-thiadiazole.

9. The product of claim 6 wherein said agent is Primene 81R amine.

10. The product of claim 5 wherein from about 5 to about 60 wt.% of said agent is used.

11. A lubricant composition comprising a major amount of an oil of lubricating viscosity or grease prepared therefrom and a minor amount of a product of reaction prepared by reacting a mercapto or dimercapto thiadiazole with a mercaptan and thionyl chloride wherein the amount of mercapto or dimercapto-thiadiazole to thionyl chloride to mercaptan varies in a molar ratio of from 1:2:1.5 to about 1:12:8 and wherein the temperature varies from 50° to about 120° C., the pressure from ambient to about 150 psi and the time from about 1 to about 8 hours or more.

12. The lubricant composition of claim 11 wherein the mercaptan is a C₁ to about a C₂₂ alkyl mercaptan.

13. The lubricant composition of claim 1 wherein the mercaptan is a tertiary alkyl mercaptan.

14. The lubricant composition of claim 13 wherein the mercaptan is t-nonyl mercaptan.

15. The lubricant composition of claim 11 wherein the reaction is carried out in the presence of a stabilizing or dispersing agent or such agent is added after the reaction is substantially completed.

16. The lubricant composition of claim 15 wherein said agent is an alkylthio-thiadiazole and a bis alkylthio-thiadiazole.

17. The lubricant composition of claim 15 wherein said agent is 2,5-bis(t-nonylthio)-1,3,4-thiadiazole.

18. The lubricant composition of claim 15 wherein said agent is Primene 81R amine.

19. The lubricant composition of claim 15 wherein from about 5 to about 60 wt.% of said agent is used.

20. The composition of claim 15 wherein the product of reaction is prepared from 2,5-dimercapto-thiadiazole, thionyl chloride and t-nonylmercaptan in the presence of 2,5-bis(t-nonylthio)-1,3,4-thiadiazole.

21. The composition of claim 15 wherein the product of reaction is prepared from 2,5-dimercapto-thiadiazole, thionyl chloride, t-nonylmercaptan and thereafter treated with Primene 81R amine.

22. The composition of claim 11 wherein said oil of lubricating viscosity is selected from mineral, synthetic and mixtures of mineral and synthetic oils.

23. The composition of claim 11 wherein said oil of lubricating viscosity is a mineral oil.

24. The composition of claim 11 wherein said oil of lubricating viscosity is a synthetic oil.

25. A zinc/phosphorus-free circulating oil or grease thereof comprising a major amount of said circulating oil and a minor amount of a product as described in claim 1.

26. A process for preparing a product of reaction comprising reacting a mercapto or dimercapto-thiadiazole, a mercaptan and thionyl chloride wherein the amount of mercapto or dimercapto-thiadiazole to thionyl chloride to mercaptan varies in a molar ratio of from 1:2:1.5 to about 1:12:8 and wherein the temperature varies from 50° to about 120° C., the pressure from ambient to about 150 psi and the time from about 1 to about 8 hours or more.

27. The process of claim 26 wherein the thiadiazole is selected from 2,5-dimercapto-1,3,4-thiadiazole.

28. The process of claim 27 wherein the thiadiazole is 2,5-dimercapto-thiadiazole.

29. The process of claim 26 wherein the mercaptan is a $C_1$–$C_{22}$ alkyl mercaptan.

30. The process of claim 27 wherein the mercaptan is t-nonylmercaptan.

31. The process of claim 26 wherein a stabilizing or dispersing agent is present in the reaction medium.

32. The process of claim 31 wherein said agent is present in an amount of from about 0.01 to about 50 wt.% of the finished blend.

33. The process of claim 26 wherein a stabilizing or dispersing agent is added after the reaction is substantially complete.

34. The process of claim 33 wherein said agent is added in an amount of from about 0.005 to about 50 wt.% based on the total weight of the finished blend.

* * * * *